United States Patent
Malon et al.

(10) Patent No.: US 8,655,035 B2
(45) Date of Patent: Feb. 18, 2014

(54) EPITHELIAL STRUCTURE DETECTOR AND RELATED METHODS

(75) Inventors: Christopher D. Malon, Fort Lee, NJ (US); Atsushi Marugame, Tokyo (JP); Eric Cosatto, Red Bank, NJ (US)

(73) Assignees: NEC Laboratories America, Inc., Princeton, NJ (US); NEC Corporation, Tokyo (JP)

( * ) Notice: Subject to any disclaimer, the term of this patent is extended or adjusted under 35 U.S.C. 154(b) by 453 days.

(21) Appl. No.: 13/105,399

(22) Filed: May 11, 2011

(65) Prior Publication Data

US 2011/0293165 A1    Dec. 1, 2011

Related U.S. Application Data

(60) Provisional application No. 61/348,322, filed on May 26, 2010.

(51) Int. Cl.
*G06K 9/00*    (2006.01)

(52) U.S. Cl.
USPC ............................ 382/128; 382/129; 382/133

(58) Field of Classification Search
USPC .......................... 382/128, 129, 133, 224–228
See application file for complete search history.

(56) References Cited

U.S. PATENT DOCUMENTS 6,026,174 A *    2/2000    Palcic et al. ................... 382/133
2004/0042646 A1*    3/2004    MacAulay et al. ........... 382/129

* cited by examiner

*Primary Examiner* — Brian Le
(74) *Attorney, Agent, or Firm* — Joseph Kolodka; Paul Schwarz

(57) ABSTRACT

A method for training a classifier to be operative as an epithelial texture classifier, includes obtaining a plurality of training micrograph areas of biopsy tissue and for each of the training micrograph areas, identifying probable locations of nuclei that form epithelia, generating a skeleton graph from the probable locations of the nuclei that form the epithelia, manually drawing walls on the skeleton graph outside of the epithelia to divide the epithelia from one another, and manually selecting points that lie entirely inside the epithelia to generate open and/or closed geodesic paths in the skeleton graph between pairs of the selected points. Data is obtained from points selected from the walls and the paths and applied to a classifier to train the classifier as the epithelial texture classifier. A method and detector for detecting epithelial structures includes applying a sample micrograph area of biopsy tissue to an epithelial texture classifier; identifying probable locations of nuclei that form epithelia of the sample micrograph area with the epithelial texture classifier, generating a skeleton graph from the probable locations of the nuclei that form the epithelia of the sample micrograph area, determining a set of open and/or closed geodesic paths in the skeleton graph of the sample micrograph area; and determining a set of the epithelial masks using the open and/or closed epithelial paths of the sample micrograph area.

24 Claims, 12 Drawing Sheets

001
111
011

EPITHELIAL STRUCTURE DETECTOR AND RELATED METHODS

RELATED APPLICATIONS

This application claims the benefit of U.S. Provisional Application No. 61/348,322, filed May 26, 2010, the entire disclosure of which is incorporated herein by reference.

FIELD

The present disclosure relates to digital pathology. More particularly, the present disclosure relates to a method for training a classifier to be operative as an epithelial texture classifier, an epithelial structure detector, and a method for detecting epithelial structures.

BACKGROUND

Relationships between nuclei within gland epithelia have diagnostic importance. For example, one marker of adenocarcinomas is a loss of epithelial polarity. Loss of polarity may be described roughly as the lack of a parallel relationship between long axes of neighboring nuclei (approximated by ellipsoids). As another example, the appearance of multilayer nuclear organization in an epithelium suggests malignancy.

The prior art has addressed the problem of distinguishing portions of tissue according to their type (epithelium, stroma, etc.) in a couple of methods. The reference entitled "Image Processing And Neural Networks For Early Detection Of Histological Changes," by J. Ramirex-Nino et al., describes a linear classifier (trained as a linear neural network) is used for classifying each pixel of the scanned image into one of four tissue categories according to its color. Then hand-designed heuristics are used to find the boundaries of the epithelium. The reference entitled, "Multifeature Prostate Cancer Diagnosis And Gleason Grading Of Histological Images," by A. Tabesh et al., describe applying a color segmentation to the tissue image and classifying each image segment as one of several different objects according to hand-designed heuristics based on its color, some basic shape features, and the earlier classification of nearby segments. One of the classes available is epithelial nuclei, which are defined as segments that have a hematoxylin color and are neither round enough to look like stromal nuclei nor large and dark enough to look like apoptotic nuclei.

Although the prior art has addressed the problem of distinguishing portions of tissue according to their type, there remains a need for an improved method for detecting epithelial structures.

SUMMARY

A method is disclosed for training a classifier to be operative as an epithelial texture classifier. The method comprises obtaining a plurality of training micrograph areas of biopsy tissue. For each of the training micrograph areas, probable locations of nuclei that form epithelia are identified and a skeleton graph from the probable locations of the nuclei that form the epithelia is generated, walls are manually drawn on the skeleton graph outside of the epithelia with a graphical user interface to divide the epithelia from one another, and points that lie entirely inside the epithelia are manually selected with the graphical user interface to generate open and/or closed geodesic paths in the skeleton graph between pairs of the selected points. Data obtained from points selected from the walls and the paths, are applied to a classifier to train the classifier as the epithelial texture classifier.

Also disclosed is method for detecting epithelial structures. The method comprises applying a sample micrograph area of biopsy tissue to an epithelial texture classifier. The epithelial texture classifier identifies probable locations of nuclei that form epithelia of the sample micrograph area. A skeleton graph is generated from the probable locations of the nuclei that form the epithelia of the sample micrograph area. A set of open and/or closed geodesic paths is determined in the skeleton graph of the sample micrograph area. A set of the epithelial masks is determined from the open and/or closed epithelial paths of the sample micrograph area.

Further disclosed is an epithelial structure detector. The epithelial structure detector comprises a processor executing instructions for: applying a sample micrograph area of biopsy tissue to an epithelial texture classifier, identifying probable locations of nuclei that form epithelia of the sample micrograph area with the epithelial texture classifier, generating a skeleton graph from the probable locations of the nuclei that form the epithelia of the sample micrograph area, determining a set of open and/or closed geodesic paths in the skeleton graph of the sample micrograph area, and determining a set of the epithelial masks using the open and/or closed epithelial paths of the sample micrograph area.

DETAILED DESCRIPTION

Figure 1:
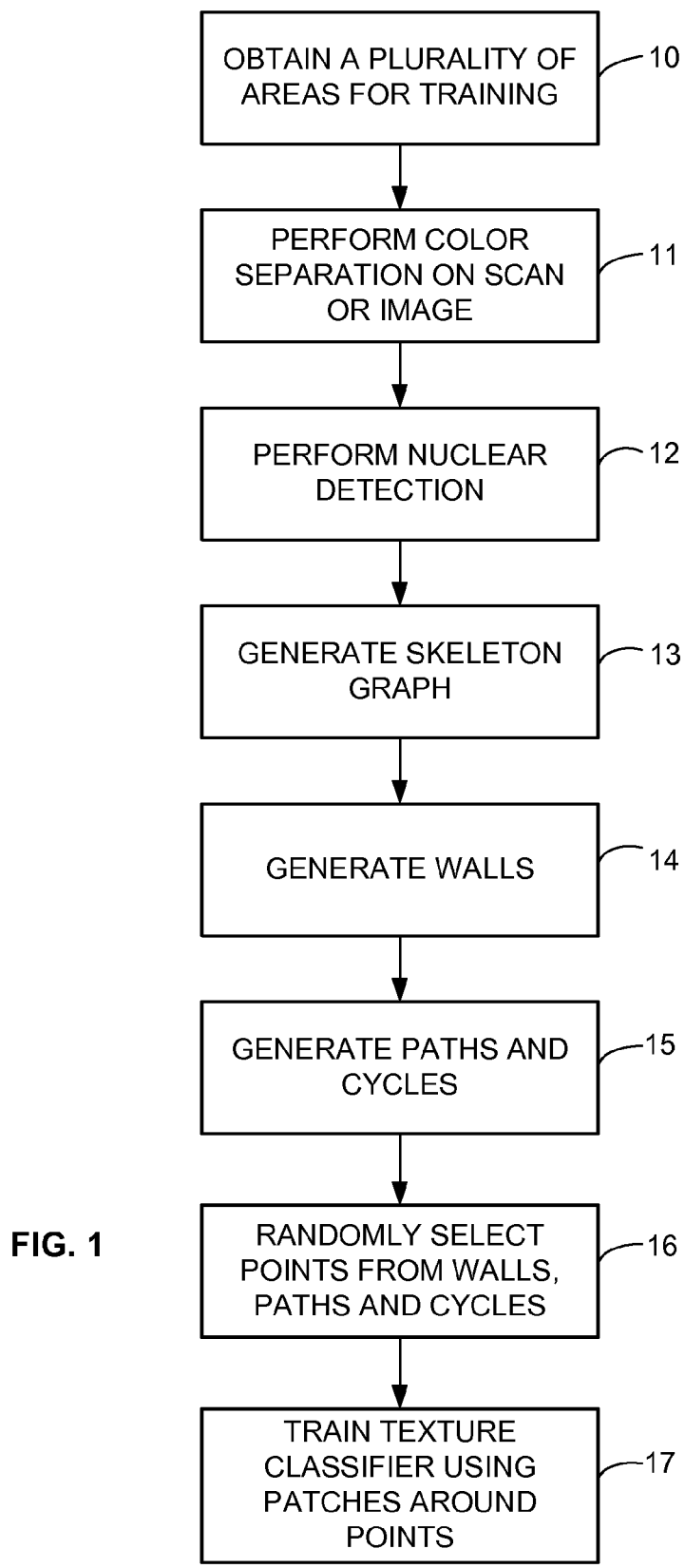
FIG. 1 is a flowchart of a method for training a classifier as an epithelial texture classifier, according to the present disclosure.

The present disclosure describes a method for training a classifier to be operative as an epithelial texture classifier. In addition, the present disclosure describes an epithelial structure detection method that produces high quality epithelial structural detections by finding the path and delimiting the area of an epithelium. The path and area can be displayed on a graphical user interface (GUI) and/or used for computing statistics about the epithelium including, without limitation, the average thickness of the epithelium, the variance of thickness of the epithelium, the variation in nuclear polarity in the epithelium, and the number of layers of nuclei in the epithelium so as to distinguish simple epithelium from stratified epithelium. The statistics about the epithelium, in turn, can be used for aiding in the diagnosis of various diseases such as cancer. For example and not limitation, the statistics can be used to distinguish situations where a nucleus is part of two fused glands (a marker of adenocarcinoma) from situations where glands are in close proximity but no nuclei are held in common. In the case of estimating the number of layers of nuclei in an epithelium, the number of nuclear intersections within a cross section inside the delimited area can be averaged throughout its epithelium. The average is a line integral over the epithelial path (which path follows the nuclei of the epithelium) and intersections are determined with respect to normal vectors along the path.

For each epithelial layer detection, the epithelial structure detector of the present disclosure outputs: 1) a binary mask over the epithelium's nuclei and 2) a path tracing the epithelium. These outputs are referred to herein as structural detections, in contrast to area detections, which indicate whether individual pixels are epithelial or not, without relationship to each other.

The present disclosure further discloses a method for transforming any area detection, other than that produced by the epithelial texture classifier into a set of structural detections. However, some area detections that are considered good might not yield good structural detections. In measuring the quality of an area detection method, typically each pixel to be classified carries equal reward or penalty, regardless of the pixel's relationship to other pixels. In the structural detection method of the present disclosure, connectivity of area detections is used. The usability of a structural detection is influenced by several factors beyond the ones that apply to area detection, including: 1) whether the structures to be detected are split into multiple pieces; whether separate structures are joined; whether non-structures are detected; and whether some structures are completely missed. The training method of the present disclosure allows for the construction of area detections that yield suitable structural detections as will be described below under the heading, "Epithelial Structure Detection."

Training

FIG. 1 is a flowchart of a method for training a classifier to be operative as an epithelial texture classifier, according to the present disclosure. The classifier can comprise without limitation a convolutional neural network (CNN), a support vector machine (SVM) or any other suitable learning machine. The structure and function of CNNs and SVMs are well known in the art. The trained epithelial texture classifier operates on a high-resolution color scan or image (i.e., a digital micrograph) of a slide of stained biopsy tissue sample. The slide with the biopsy tissue sample may be prepared by staining the tissue sample with multiple dyes, each of a different color, and then an imaging device can be used for obtaining a color scan or image (the digital micrograph) of the slide of the stained biopsy tissue sample. The biopsy tissue is stained with different stains that make the shape of the nuclei and the epithelia apparent. In one exemplary embodiment, the stains used for staining the biopsy tissue can include hematoxylin and eosin.

In block 10 of FIG. 1, a plurality of slide micrograph areas are obtained for use in training the classifier. The slide micrograph areas (training set) can be obtained from a micrograph of a single slide or from micrographs of multiple slides. In one exemplary embodiment, the areas can have a size of 1024 by 1024 pixels at 20× magnification. In other embodiments, depending on the resources available and quality requirements, areas having other sizes and/or magnifications can be used.

In block 11, the areas of the training set are applied as input to a color transformer. The color transformer performs a color transformation or separation process on each pixel of each area in order to separate the corresponding image into one or more color channels, where each color channel corresponds to the color of one of the dyes and provides information about the density of each dye at each pixel. In one exemplary embodiment, the color channels correspond to the colors of the hematoxylin and eosin dyes if the hematoxylin and eosin dyes were used for staining the biopsy tissue and the intensity of each pixel in a channel indicates the estimated density of the corresponding dye. A further description of such a color transformation process, can be found for example, in U.S. application Ser. No. 12/131,346 filed Jun. 2, 2008. The disclosure of U.S. application Ser. No. 12/131,346, as it relates to the color transformation process, is incorporated herein by reference. In an alternative embodiment, the color channels may be a red, green, and blue color separation, which provides information about the density of red, green, and blue at each pixel.

In block 12, a nuclear detection process is performed in the color channels for each of the areas of the training set, to identify probable locations of nuclei that form the epithelium. In the nuclear detection process each pixel of each area is classified as nuclear or not based on its color. In one exemplary embodiment, the pixels of the areas can be classified using a trained support vector machine. For each area, the pixels classified or detected as nuclear, are then filtered based on the size of a four-connected region (i.e., a region including a given pixel, a pixel to the left of the given pixel, a pixel to the right of the given pixel, a pixel up from the given pixel and a pixel down from the given pixel) to which they belong to produce a first binary image, which classifies each pixel as nuclear or not. Next, a box average of the first binary image is computed over a 24×24 pixel region, where the box average B of an image P is $$B(x, y) = \frac{1}{(2k+1)^2} \sum_{t=-k'}^{k'} \sum_{j=-k'}^{k'} P(x+t, y+j)$$

where x and y are coordinates of the image and k describes the width of the box average. Finally, this box average is filtered to select pixels where the response is greater than 0.01 (pixel values can be fractional between 0 and 1, not just 0 or 1), producing again a second binary image. The second binary image may be interpreted as a selection of pixels that are near a nuclear pixel, and is referred to herein as an image of blurred nuclear detections.

In block 13, for each area, a thinning algorithm is applied to the corresponding image of blurred nuclear detections, to produce a skeleton image of the blurred nuclear detection image. Any binary image, such as the skeleton image, defines an undirected graph called a Path Junction Graph, which we define as follows. Each positive pixel in the binary image is labeled with the number of positive pixels it is 4-adjacent to. The positive pixels that are connected to exactly two positive neighbors are referred to herein as path pixels and the other positive pixels are referred to as junction pixels. Each 4-connected component of path pixels is referred to herein as a path. To define an undirected graph, a vertex set and an edge set must be defined. Accordingly, the set of paths define the edge set and the set of junction pixels define the vertex set of the undirected graph. We refer to this undirected graph as the Path Junction Graph of the binary image. We call the Path Junction Graph of the skeleton image the Skeleton Graph.

Figures 7, 8:
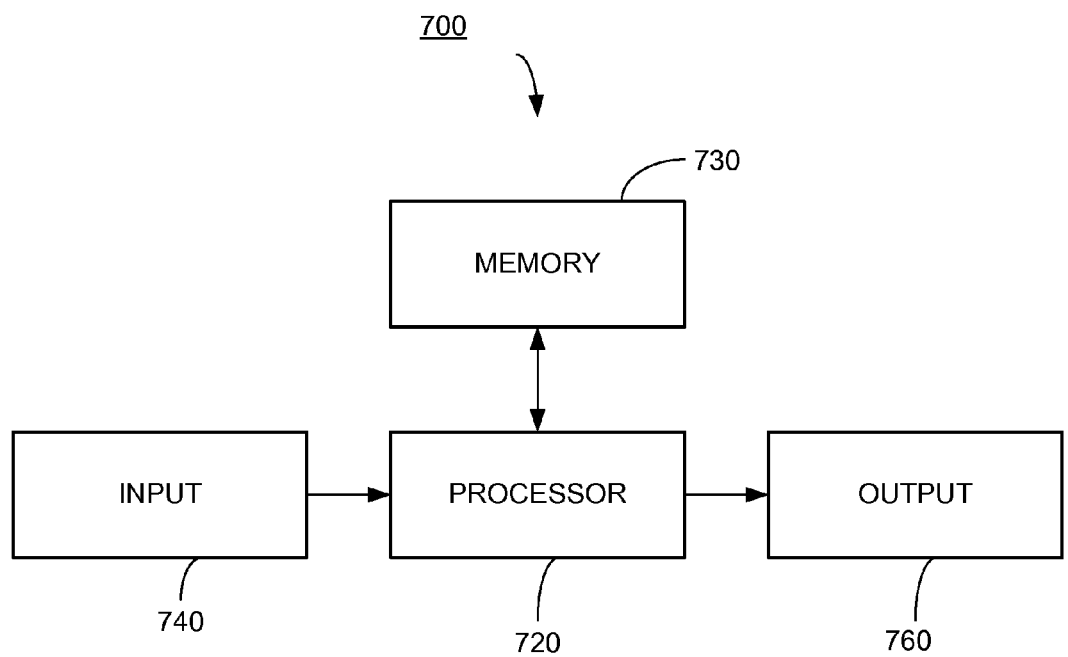
FIG. 7 is a block diagram of an exemplary embodiment of a computer system for implementing the methods described herein.
FIG. 8 is a diagram of a 3×3 binary image illustrating a 4-connected component of path pixels.

FIG. 8 is an example of a 3×3 binary image illustrating a 4-connected component of path pixels depicted with 0 or 1, where the center pixel (1) is 4-adjacent to three other pixels, i.e., the pixel (1) directly to the left of the center pixel, the pixel (1) directly to the right of the center pixel and the pixel (1) directly below the center pixel.

Figure 3A:
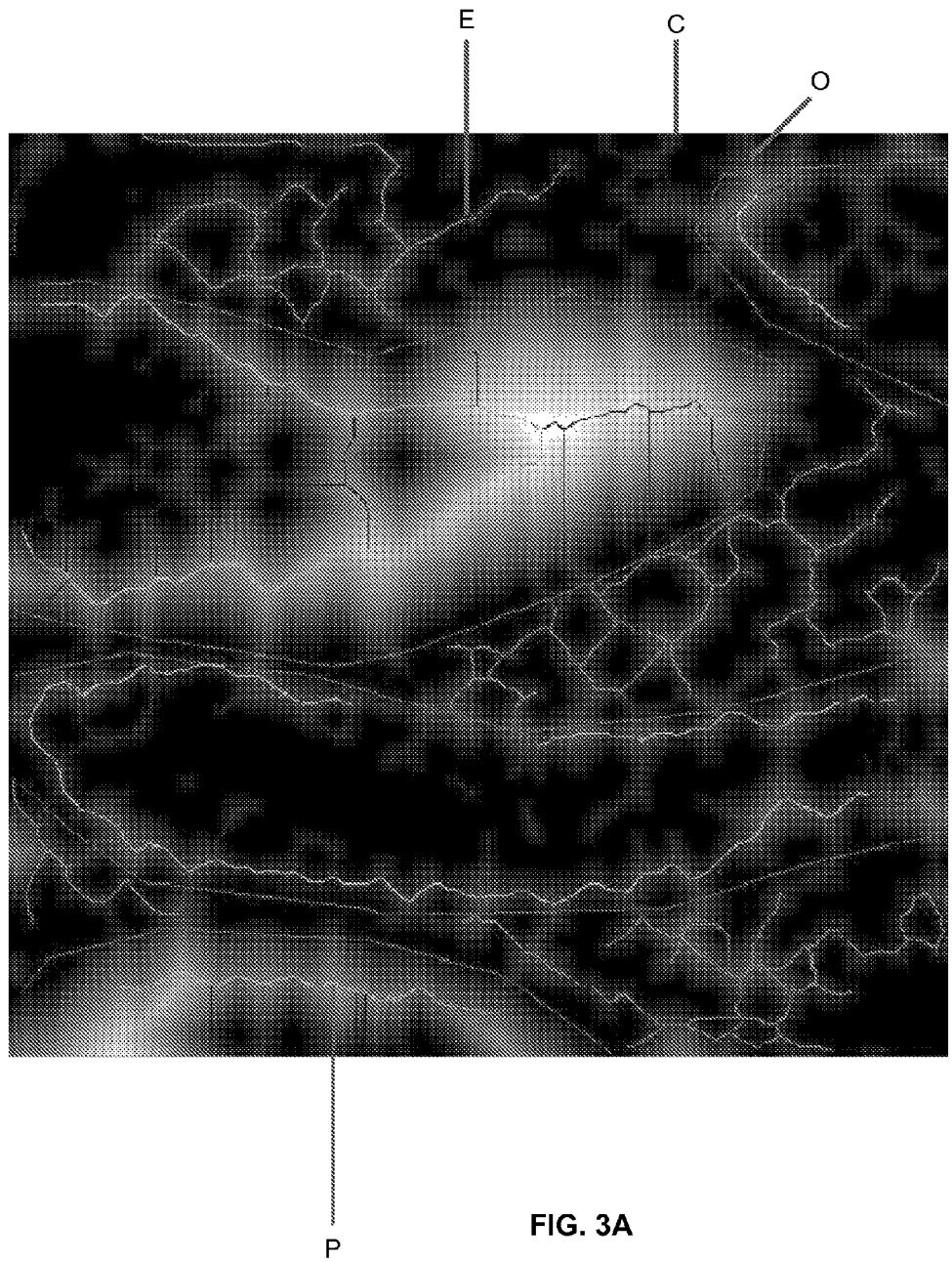
FIGS. 3A and 4A are skeleton graphs of two different exemplary areas of an exemplary training set produced by a thinning process, illustrating walls drawn by the user, paths and loops selected by the user that trace epithelial paths within the skeleton, and other edges in the skeleton.
Figure 4A:
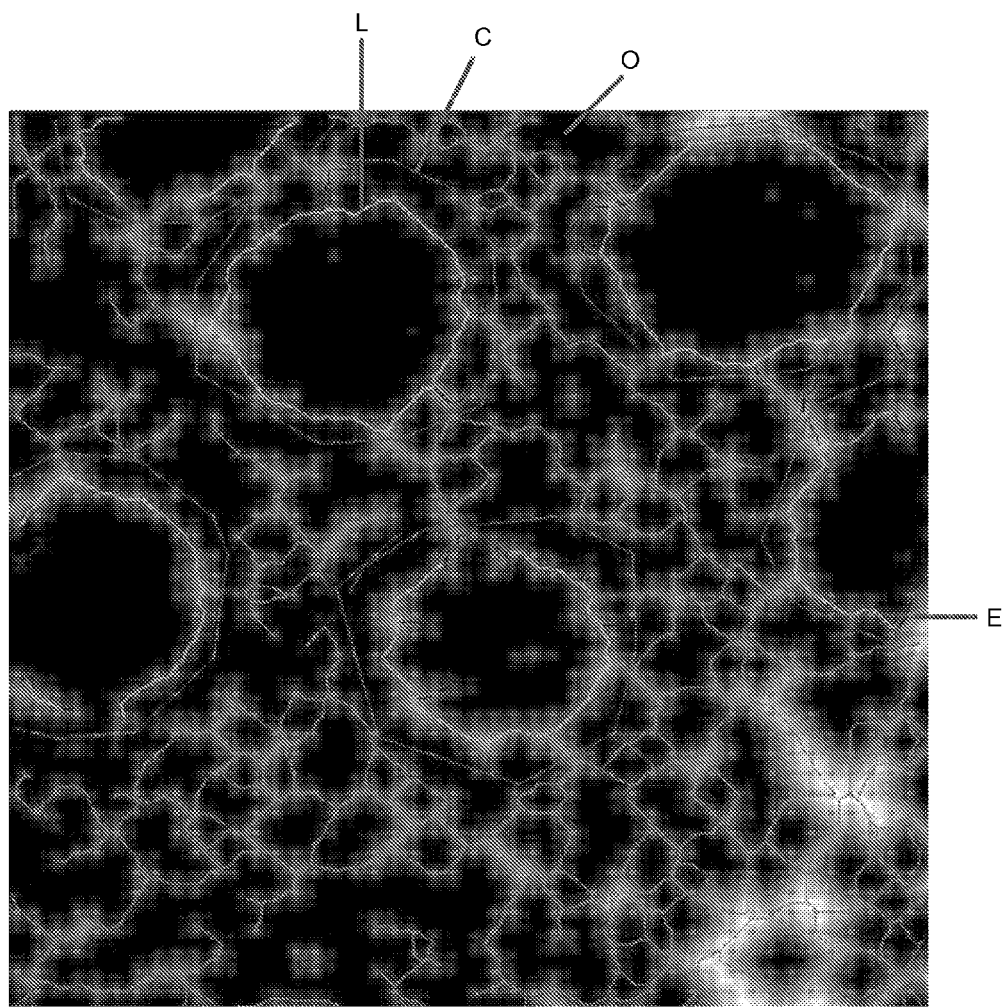

Any Path Junction Graph is naturally weighted, with the weight of an edge being the number of path pixels associated to the corresponding path. FIGS. 3A and 4A illustrate skeleton graphs of two different exemplary areas of an exemplary training set. In one exemplary embodiment, the thinning algorithm can be a Hilditch thinning algorithm which produces a Hilditch skeleton.

Figure 3B:
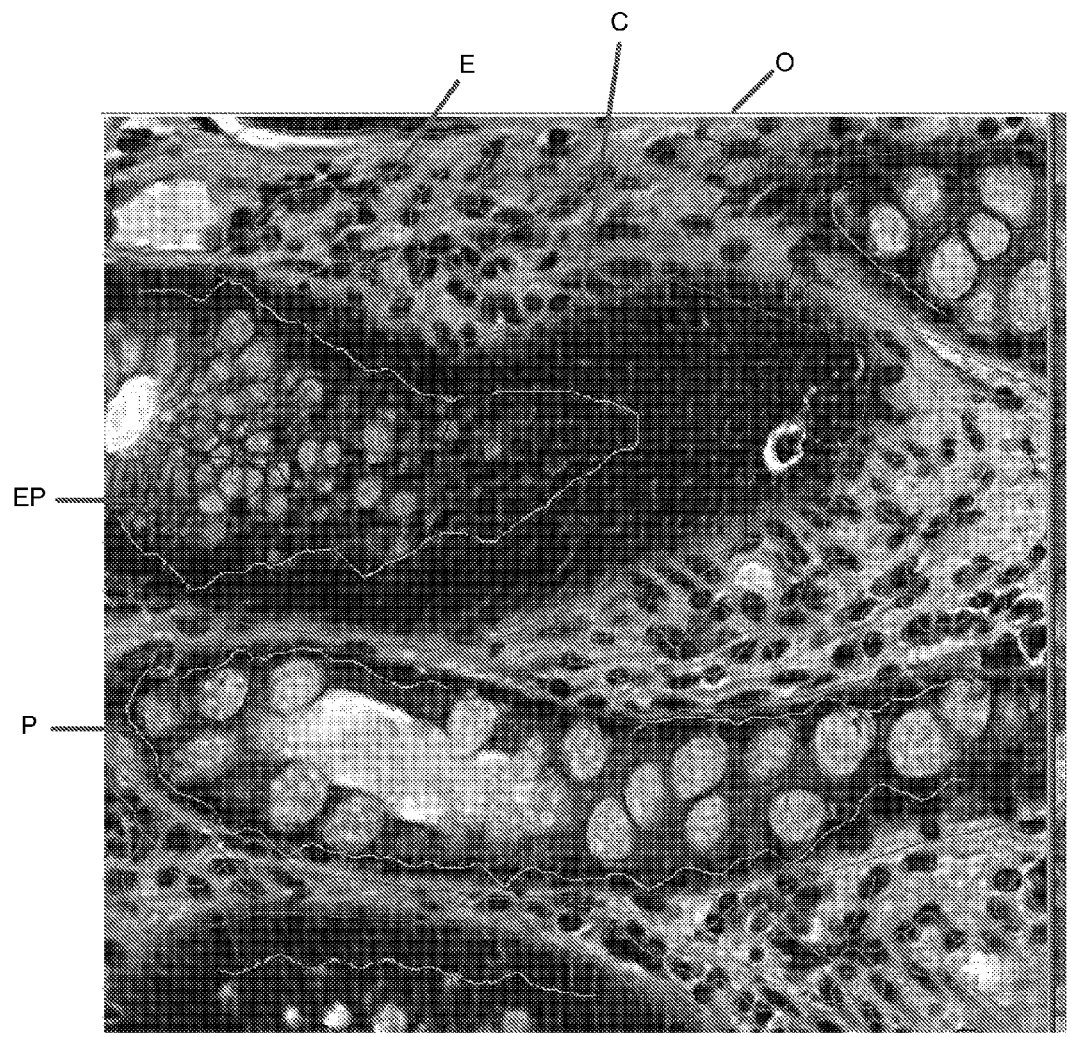
FIGS. 3B and 4B show the skeleton graphs of FIGS. 3A and 3B laid over the original images of the two different areas of the training set.
Figure 4B:
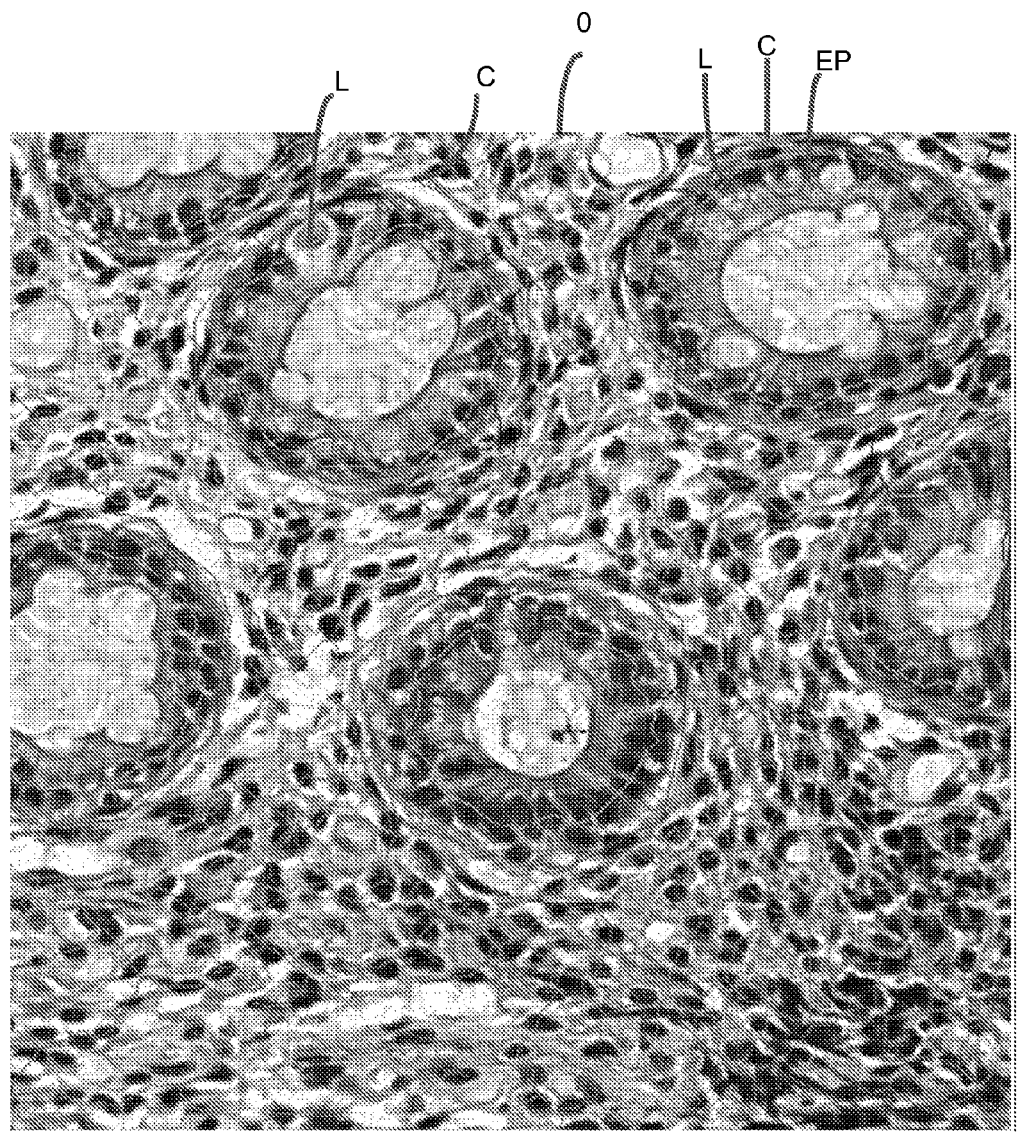

Referring collectively to FIGS. 1, 3A, 3B, 4A, and 4B, in block 14, curves C are manually drawn by a user or operator on the skeleton graph of the blurred nuclear detection image as shown in FIGS. 3B and 4B. This step is performed by drawing the curves C on the original image O (FIGS. 3A and 3B) of the area using a GUI. Each curve is drawn completely outside of an epithelium EP. A sufficient number of curves C are drawn so as to cut every edge E of the skeleton of the blurred nuclear detection image that passes between the inside and outside of an epithelium EP such that the curves C represent walls dividing the epithelium EP.

Referring still to FIGS. 1, 3A, 3B, 4A, and 4B, in block 15, the GUI removes edges E of the skeleton graph of the blurred nuclear detection image that cross the walls formed by the curves C, The operator uses the GUI to manually select open paths (paths P) and closed paths (cycle or loops L) within the remaining edges E of the skeleton. The paths P and loops L are selected so that they lie entirely inside the epithelium EP and follow the direction of the membranes, i.e., the paths and loops connect the nuclei of the epithelium thereby tracing the epithelium.

In one exemplary embodiment, the paths and loops are selected using a GUI that is configured to find the shortest path in the skeleton graph between two user-selected junctions (points selected in the original image that lie entirely inside epithelium). The shortest path is referred herein to as a geodesic path.

The concept of a geodesic path as used in the present disclosure is the one from graph theory, i.e., any path in the graph that represents the shortest path in the graph between its two endpoints. In the present disclosure, a geodesic loop at a vertex A in a path junction graph G is defined to be a geodesic path P from vertex A to some vertex B in graph G, concatenated with a geodesic path from vertex B to vertex A in G', where G' is the subgraph that remains after removing each edge of geodesic path P from graph G.

In block 16, points are randomly selected by the GUI from the walls, which points are outside the epithelia and considered negative training data, and points are randomly selected from the paths and loops, which points are within the epithelia and considered positive training data. A patch is sampled around each selected point on the walls, paths, and loops. In one exemplary embodiment, the patches measure 64×64 pixels at 20× magnification.

In block 17, the data obtained from each of the patches is used for training the classifier to be operative as an epithelial texture classifier. In one exemplary embodiment, the classifier can comprise the CNN shown in FIG. 6 and described below. In embodiments where hematoxylin and eosin dyes are used for staining the biopsy tissue, the epithelial texture classifier can use color channels corresponding to the hematoxylin and eosin dyes as input. Alternative embodiments of the epithelial texture classifier can use other desired color channels.

Figure 6:
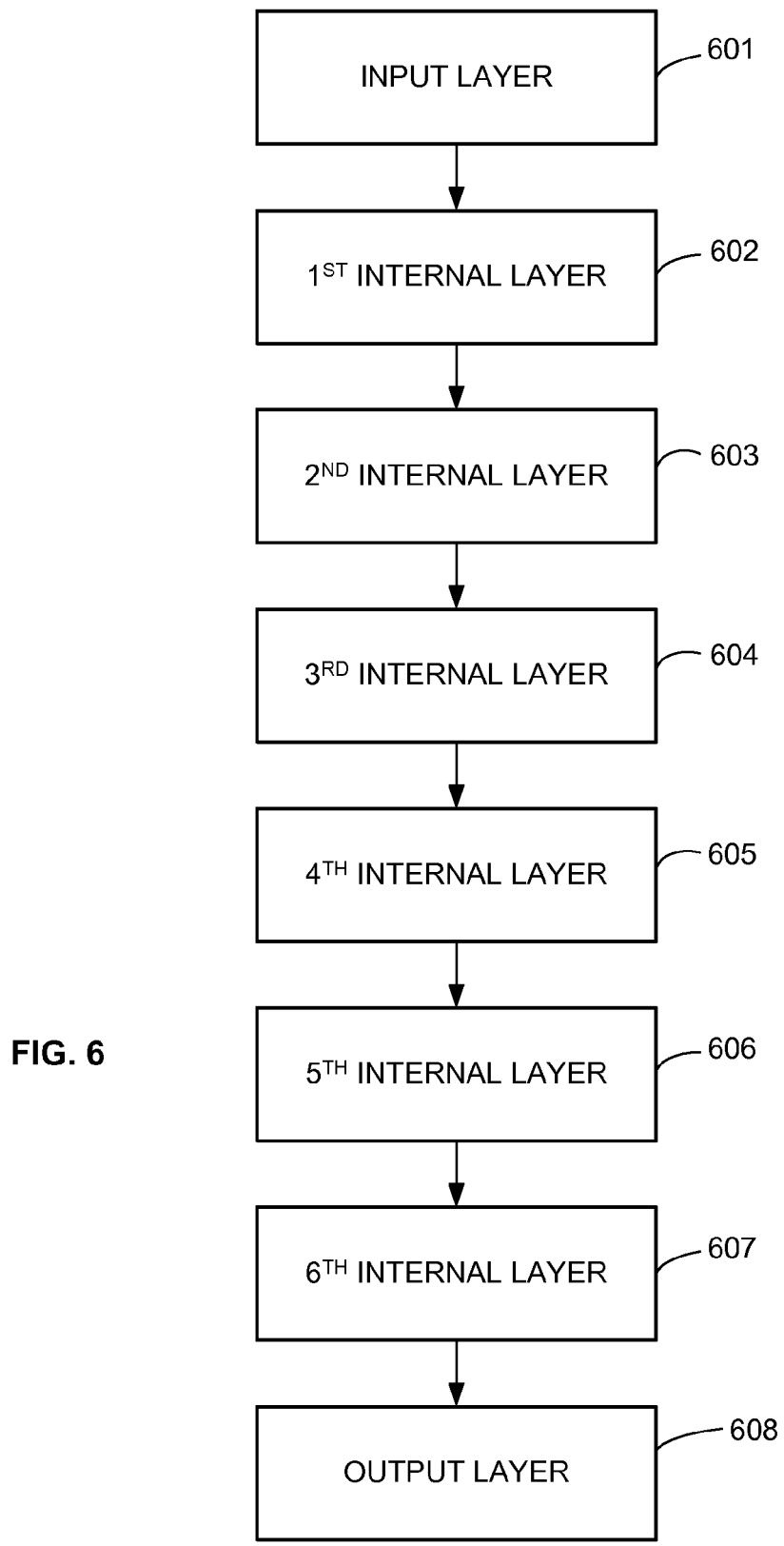
FIG. 6 is a block diagram of an exemplary embodiment of a convolutional neural network that when trained according to the present disclosure, will be operative as an epithelial texture classifier.

FIG. 6 schematically depicts an exemplary embodiment of a CNN that when trained according the present disclosure, will be an epithelial texture classifier. The CNN includes an input layer 601, first, second, third, fourth, fifth, and sixth internal layers 602, 603, 604, 605, 606, and 607, respectively, and an output layer 608. The CNN convolves a stack of inputs 601 (input layer), referred to as feature maps, with small filters 602 to obtain a new stack of feature maps, referred to as an internal layer or first internal layer 603. The input layer 601 includes two (2) feature maps. In one exemplary embodiment, one of the two feature maps estimates hematoxylin density and the other one of the two feature maps estimates eosin density. The first internal layer 602 includes eight (8) feature maps, which are obtained by convolving the two input feature maps with 5×5 kernels, adding a constant offset, and computing a hyperbolic tangent of the result. The values of the kernels and the constant offsets are obtained by the training process described above. Because there are 8 feature maps in the first internal layer 602, there are 16 kernels and 8 constant offsets that must be trained. Because of the 5×5 convolution, each of the 8 feature maps in the first internal layer 602 is 4 pixels smaller in both x and y than each of the two feature maps in the input layer 601.

The second internal layer 603 is obtained by subsampling. Every 2×2 group of values in each of the 8 feature maps outputted from the first internal layer 602 is averaged together, multiplied by a constant, offset by another constant, and passed through the hyperbolic tangent function. This is performed separately for each of the 8 feature maps at the output of the first internal layer 602. Accordingly, the second internal layer 603 includes 8 feature maps each of which is computed from one of the 8 feature maps at the output of the first internal layer 602. The corresponding 8 multipliers and 8 offsets are obtained by training. Each of the 8 feature maps in the second internal layer 603 is half the width and half the height of their corresponding 8 feature maps in the first internal layer 602.

The third internal layer 604 has eight (8) feature maps, which are obtained by convolution with 5×5 kernels, offsetting with constants, and passing the result through the hyperbolic tangent function, in the same manner as described with respect to the first internal layer 602. Each of the 8 feature maps is computed from the 8 feature maps outputted from the second internal layer 603, therefore, there are 64 kernels to be trained.

The fourth internal layer 605 is computed by subsampling in the same manner as described with respect to the second internal layer 603. Therefore, the fourth internal layer includes 8 feature maps, each of which is obtained from one of the 8 feature maps at the output of the third internal layer 604.

The fifth layer 606 includes 16 feature maps, which are obtained by convolution with 7×7 kernels, offsetting with constants, and passing the result through the hyperbolic tangent function, in the same manner as described with respect to the first internal layer 602. Because each of the 16 feature maps is computed from the 8 feature maps at the output of the fourth internal layer 605, there are 128 kernels to be trained.

The sixth internal layer 607 includes 16 feature maps obtained by convolution with 7×7 kernels, offsetting with constants, and passing the result through the hyperbolic tangent function, in the same manner as the first internal layer 602. Because each of the 16 feature maps is computed from the 16 feature maps at the output of the fifth internal layer 607, there are 256 kernels to be trained.

The output layer 608 includes 2 feature maps. One of these 2 output layer feature maps is trained to have a large value when the input window is selected from a path or cycle generated in step 13, and the other one of the 2 output layer feature maps is trained to have a large value when the input window is selected from a wall generated in step 14. The 2 output layer feature maps are obtained by convolution with 1×1 kernels, so that each output of the output layer 608 is just a weighted sum of corresponding values in all the 16 feature maps at the output of the sixth internal layer 607, with the weights obtained by training. With this architecture, each output value depends on a 64×64 window.

Epithelial Structure Detection

Figure 5:
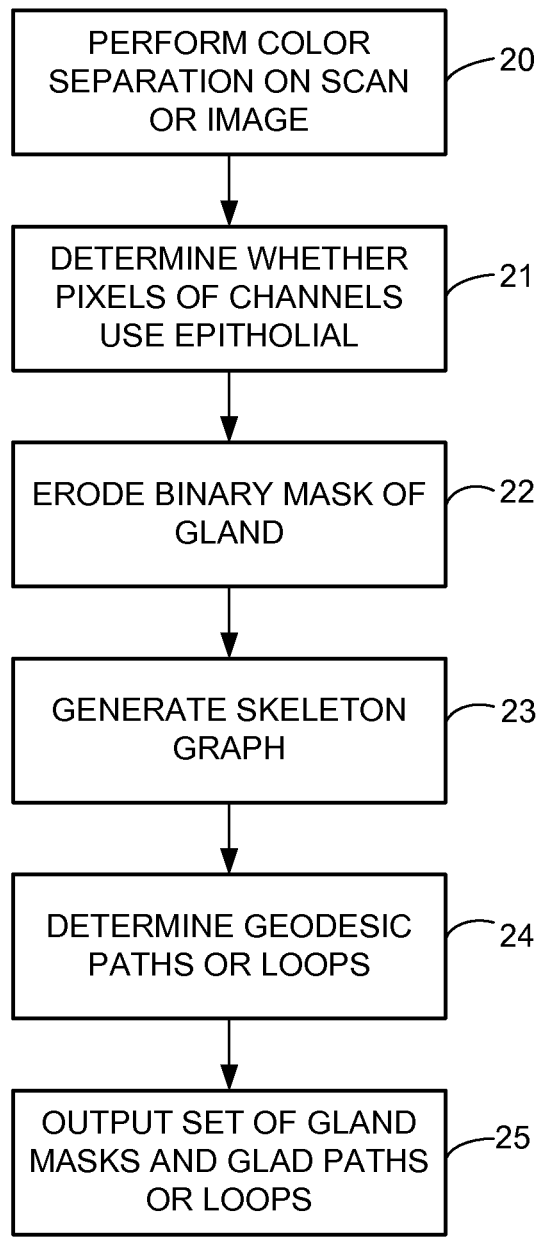
FIG. 5 is a flowchart of an epithelial structure detection method of the present disclosure.

FIG. 5 is a flowchart of an epithelial structure detection method performed by an epithelial structure detector. An integral component of the epithelial structure detector is the epithelial texture classifier described above. To find epithelial paths (a path through an epithelium traverses the epithelium's nuclei) in a given area of a high-resolution color scan or image of a digital micrograph, the method commences in block 20 with a color separation process identical to that used in the training method. For example, this process may separate the image into channels corresponding to the colors of the hematoxylin and eosin dyes.

In block 21, the output of the color separation process is used as input to the epithelial texture classifier component of the detector. The epithelial texture classifier produces a decision for each pixel as to whether it is part of an epithelium or not. These decisions may be encoded as a binary image or binary mask in which pixel values are zero (0) or one (1), according to whether the decision is negative or affirmative. In one embodiment, a pixel value is designated as a one (1) when the decision is affirmative. In an alternate embodiment, a pixel value is designated as a zero (0) when the decision is affirmative.

Optionally in block 22, the binary mask from the previous step may be eroded to produce a new binary mask (eroded epithelium or gland mask). In an exemplary embodiment, the detector calculates a three (3) by three (3) box average around each pixel in the binary output of the epithelial texture classifier to erode the binary mask, and points where the box average is positive are taken to be the positive points in the eroded gland mask. Note that other box average sizes may be used.

In block 23, the detector generates a skeleton graph by applying a thinning algorithm to the binary mask or the eroded gland mask, which produces a skeleton image of the mask. In one exemplary embodiment, the thinning algorithm can be a Hilditch thinning algorithm. The detector then computes a path junction graph of the skeleton image which results in the skeleton graph. As described earlier, the path junction graph is an undirected graph, in which the set of paths is regarded as an edge set and the set of junction pixels is regarded as the vertex set. The graph is naturally weighted, with the weight of an edge being the number of path pixels associated to the corresponding path. Using these weights, the detector computes the distances and shortest paths between every pair of vertices.

In block 24, the epithelial structure detector determines a set of geodesic paths or geodesic loops. The detector repeatedly utilizes the following geodesic search step to find a geodesic path or geodesic loop in a path junction graph G, assuming the set of edges in G is non-empty. First, the detector finds the longest geodesic path P in the graph G. Then it deletes the edges in P from G, forming a subgraph G'. Let d be the total distance along P. If there are two vertices A and B along P whose geodesic distance in G' is greater than d, then the geodesic path P' from A to B in G' is concatenated to the subpath of P from B to A, and the resulting geodesic loop is returned. Otherwise, the geodesic path P is returned.

It is well known that the distance transform of a binary mask is a bitmap whose pixel values are non-negative integers defined by associating to each pixel the taxicab distance, a.k.a. rectilinear distance (e.g. see http://en.wikipedia.org/wiki/Taxicab_distance) in the bitmap to the nearest non-positive pixel. In particular, the map assigns every non-positive pixel to zero. The epithelial structure detector produces a set of geodesic paths or loops by initially computing the distance transform D of the gland mask or eroded gland mask E, and assigning $E_1 = E$. At step i, the detector computes the path junction graph $G_i$ of the skeleton image of the binary mask $E_i$, terminating if $G_i$ has no edges. Then the detector applies the geodesic search step to graph $G_i$, obtaining the longest geodesic epithelial path or geodesic epithelial loop $P_i$ in $G_i$. From the epithelial paths and loops $P_i$, the detector computes an epithelial mask $M_i$ by taking the union of all pixels within rectilinear distance D(x, y) of each pixel (x, y) along $P_i$, where D(x, y) is the value of a distance transform at (x, y). Then $E_{i+1}$ is formed by erasing $M_i$ from $E_i$ (setting all pixels in $M_i$ to zero). Unless a stopping condition (for example, a length requirement for the epithelial paths and loops $P_i$) is satisfied, the detector proceeds with another iteration.

In block 25, the epithelial structure detector outputs a set of the epithelial masks $M_i$ and epithelial paths and loops $P_i$ that have been computed.

Figure 2A:
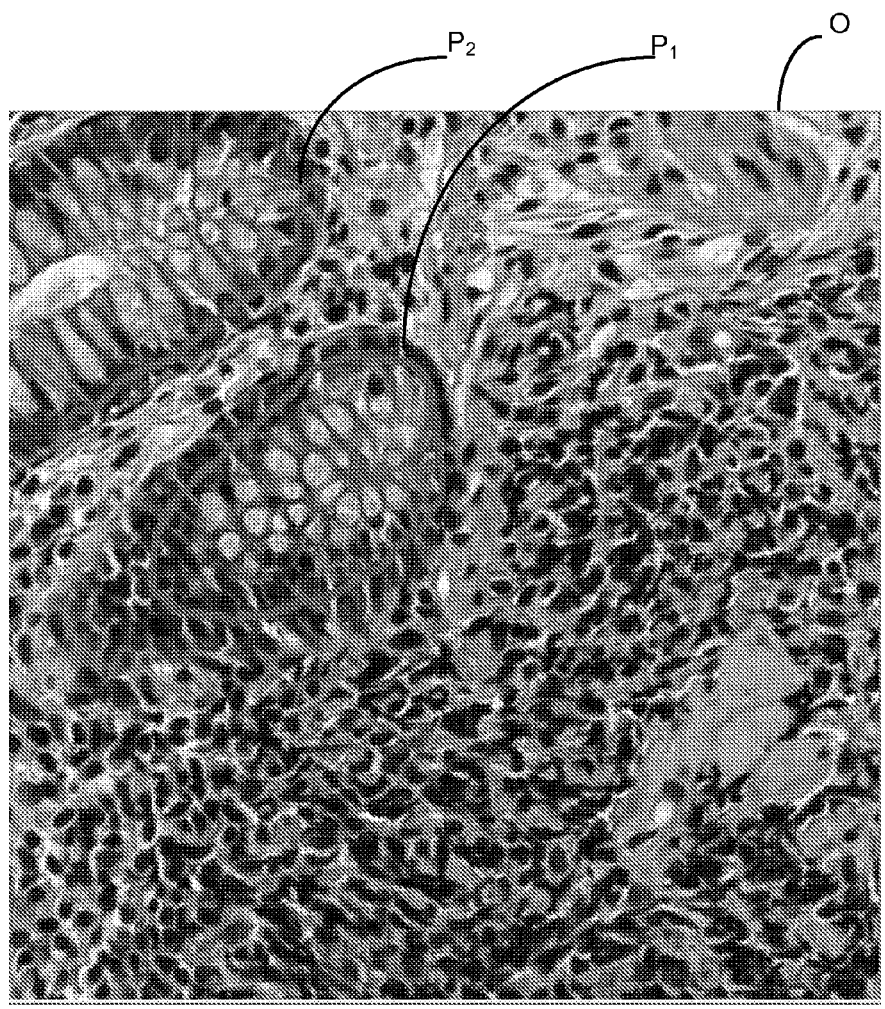
FIG. 2A illustrates an exemplary mask outputted by the epithelial structure detection method of the present disclosure which comprises open and closed epithelial paths marked on a high-resolution image or scan of a section of a hematoxylin and eosin stained colon tissue sample which image or scan was used as an input to the epithelial texture classifier.
Figure 2B:
FIG. 2B illustrates an inversion of the mask outputted by the epithelial structure detection method of the present disclosure in FIG. 2A, overlaid on top of the original image.
Figure 2C:
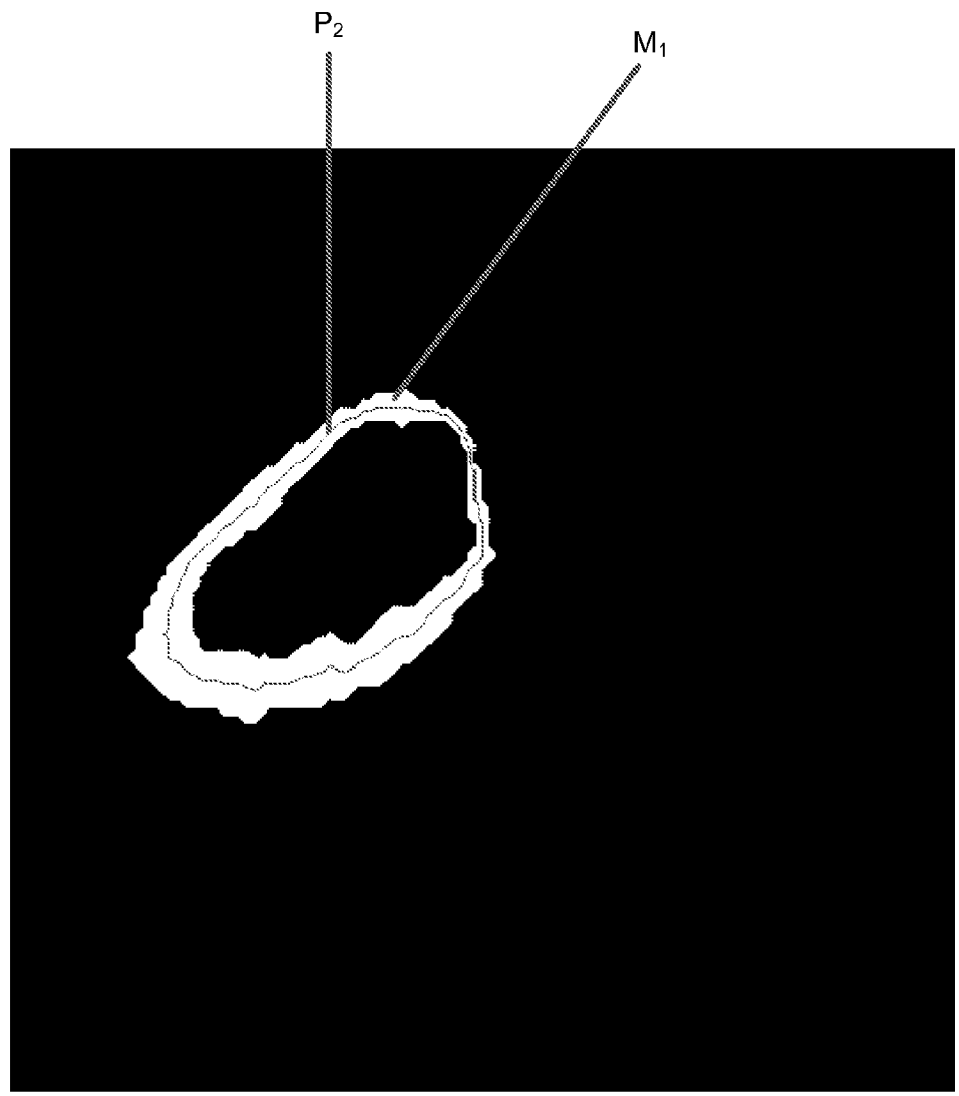
FIG. 2C illustrates the loop $P_1$ shown in FIGS. 2A and 2B, and mask $M_1$.
Figure 2D:
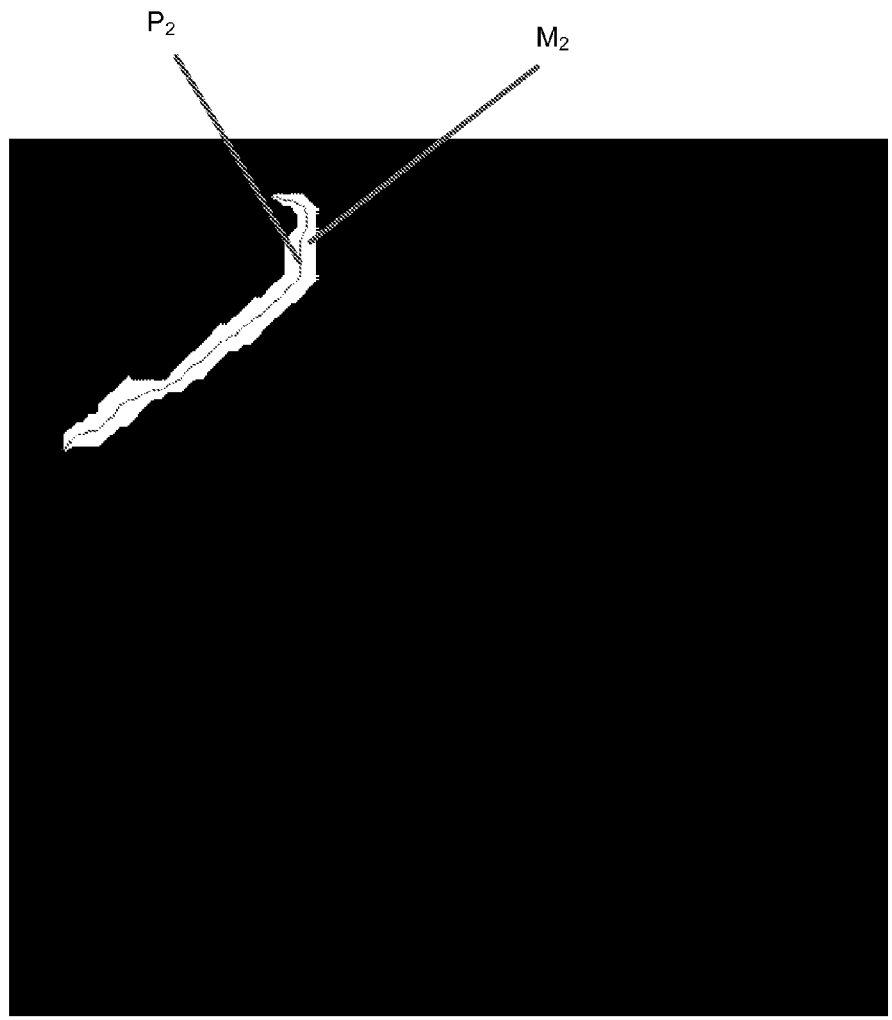
FIG. 2D illustrates the path $P_2$ shown in FIGS. 2A and 2B, and mask $M_2$.

FIG. 2A illustrates an epithelial loop $P_1$ and an epithelial path $P_2$ output by the epithelial structure detector in block 26 and laid over the original image O (area). FIG. 2B illustrates an inversion of the mask (inverted mask IM) produced by the trained epithelial texture classifier in block 21, laid over the original image O, used to produce the epithelial path $P_2$ and the epithelial loop $P_1$ output by the detector in block 26. The loop $P_1$ and mask $M_1$ are shown in FIG. 2C. The path $P_2$ and mask $M_2$ are shown in FIG. 2D.

FIG. 7 is a block diagram of an exemplary embodiment of a computer system 700 for implementing the epithelial structure detector and methods described herein. The computer system 700 includes at least one processor 720, at least one memory 730 for storing one or more programs which are executable by the processor(s) 720 for implementing the epithelial structure detector and methods described herein, one or more inputs 740 for receiving input data, e.g., color scan or image data, data from the GUI, etc., and an output 760 for outputting data, e.g., the epithelial structure detector outputs the set of epithelial masks $M_i$ and epithelial paths and loops $P_i$ that have been computed.

While exemplary drawings and specific embodiments of the present disclosure have been described and illustrated, it is to be understood that that the scope of the invention as set forth in the claims is not to be limited to the particular embodiments discussed. Thus, the embodiments shall be regarded as illustrative rather than restrictive, and it should be understood that variations may be made in those embodiments by workers skilled in the arts without departing from the scope of the invention as set forth in the claims that follow and their structural and functional equivalents.

What is claimed is:

1. A computer implemented method for training a classifier to be operative as an epithelial texture classifier, the method comprising the steps of:
obtaining a plurality of training micrograph areas of biopsy tissue;
for each of the training micrograph areas:
identifying probable locations of nuclei that form epithelia;
generating a skeleton graph from the probable locations of the nuclei that form the epithelia;
with a graphical user interface, manually drawing walls on the skeleton graph outside of the epithelia to divide the epithelia from one another;
with the graphical user interface, manually selecting points that lie entirely inside the epithelia to generate open and/or closed geodesic paths in the skeleton graph between pairs of the selected points;
and
applying data obtained from points selected from the walls and the paths to a classifier to train the classifier as the epithelial texture classifier;
wherein the probable locations of nuclei identified with an epithelial texture classifier are outputted as an epithelial mask and wherein the generation of the skeleton graph from the probable locations of the nuclei that form the epithelia of the sample micrograph area includes:
determining a skeleton image of the epithelial mask;
determining a path junction graph of the skeleton image;
stopping if the path junction graph has no edges;
applying to the path junction graph, the determination of the set of geodesic paths and/or loops in the skeleton graph to determine the epithelial paths and/or loops; and
taking an area of a distance transform of the epithelial mask around the open and/or closed epithelial paths to determine the epithelial mask.

2. The method according to claim 1, wherein the biopsy tissue is stained with one or more dyes and for each of the micrograph areas, further comprising the step of separating the micrograph area into one or more color channels, where each color channel corresponds to the color of the one or more dyes, prior to the identifying of the probable locations of the nuclei that form the epithelia.

3. The method according to claim 1, wherein the identifying step includes the step of classifying each pixel of the training micrograph as a probable nuclear location or not based on its color.

4. The method according to claim 1, wherein the identifying step includes the step of determining probable nuclear locations using erosion of the output of a classification of each pixel based on its color.

5. The method according to claim 1, wherein the step of generating the skeleton graph includes the step of applying a thinning process to the probable nuclear locations to generate a skeleton image of probable nuclear locations.

6. The method according to claim 5, wherein the thinning process comprises a Hilditch thinning process.

7. A computer implemented method for detecting epithelial paths in a sample micrograph area of biopsy tissue, the method comprising the steps of:
applying an epithelial texture classifier to the sample micrograph area of biopsy tissue identifying probable locations of nuclei that form epithelia of the sample micrograph area with the epithelial texture classifier;
generating a skeleton graph from the probable locations of the nuclei that form the epithelia of the sample micrograph area; and
determining a set of geodesic paths and/or geodesic loops in the skeleton graph of the sample micrograph area;
wherein the probable locations of nuclei identified with an epithelial texture classifier are outputted as an epithelial mask and wherein the generation of the skeleton graph from the probable locations of the nuclei that form the epithelia of the sample micrograph area includes:
determining a skeleton image of the epithelial mask;
determining a path junction graph of the skeleton image;
stopping if the path junction graph has no edges;
applying to the path junction graph, the determination of the set of geodesic paths and/or loops in the skeleton graph to determine the epithelial paths and/or loops; and
taking an area of a distance transform of the epithelial mask around the open and/or closed epithelial paths to determine the epithelial mask.

8. The method according to claim 7, further comprising the step of determining a set of the epithelial masks using the probable locations of nuclei and the geodesic paths and/or geodesic loops of the sample micrograph area.

9. The method according to claim 7, wherein the identifying step includes classifying each pixel of the sample micrograph as a probable nuclear location or not based on its color.

10. The method according to claim 7, wherein the identifying step includes determining probable nuclear locations using erosion of the output of a classification of each pixel based on its color.

11. The method according to claim 7, wherein the identifying step includes classifying each pixel as a probable location of a nuclei in an epithelium or not.

12. The method according to claim 7, wherein the identifying step includes determining probable nuclear locations using erosion of the output of the epithelial texture classifier.

13. The method according to claim 7, wherein the biopsy tissue is stained with one or more dyes and for each of the micrograph areas, further comprising the step of separating the micrograph area into one or more color channels, where each color channel corresponds to the color of the one or more dyes, prior to the step of identifying of the probable locations of the nuclei that form the epithelia.

14. The method according to claim 7, wherein the step of generating the skeleton graph includes applying a thinning process to the probable nuclear locations to generate a skeleton image of the probable nuclear locations.

15. The method according to claim 14, wherein the thinning process comprises a Hilditch thinning process.

16. An epithelial structure detector comprising:
a processor executing instructions for:
applying an epithelial texture classifier to a sample micrograph area of biopsy tissue;
identifying probable locations of nuclei that form epithelia of the sample micrograph area with the epithelial texture classifier;
generating a skeleton graph from the probable locations of the nuclei that form the epithelia of the sample micrograph area; and
determining a set of geodesic paths and/or geodesic loops in the skeleton graph of the sample micrograph area;
wherein the probable locations of nuclei identified with the epithelial texture classifier are outputted as an epithelial mask and wherein the generation of the skeleton graph from the probable locations of the nuclei that form the epithelia of the sample micrograph area includes:

determining a skeleton image of the epithelial mask;
determining a path junction graph of the skeleton image;
stopping if the path junction graph has no edges;
applying to the path junction graph, the determination of the set of geodesic paths and/or loops in the skeleton graph to determine the epithelial paths and/or loops; and
taking an area of a distance transform of the epithelial mask around the open and/or closed epithelial paths to determine the epithelial mask.

17. The detector according to claim 16, further comprising instructions for determining a set of the epithelial masks using the probable locations of nuclei and the geodesic paths and/or geodesic loops of the sample micrograph area.

18. The detector according to claim 16, the identifying instruction includes classifying each pixel of the sample micrograph as a probable nuclear location or not based on its color.

19. The detector according to claim 16, wherein the identifying instruction includes determining probable nuclear locations using erosion of the output of a classification of each pixel based on its color.

20. The detector according to claim 16, wherein the identifying instruction includes classifying each pixel as a probable location of a nuclei in an epithelium or not.

21. The detector according to claim 16, wherein the identifying instruction includes determining probable nuclear locations using erosion of the output of the epithelial texture classifier.

22. The detector according to claim 16, wherein the biopsy tissue is stained with one or more dyes and for each of the micrograph areas, further comprising the instructions for separating the micrograph area into one or more color channels, where each color channel corresponds to the color of the one or more dyes, prior to the identifying of the probable locations of the nuclei that form the epithelia.

23. The detector according to claim 16, wherein the instructions for generating the skeleton graph includes applying a thinning process to the probable nuclear locations to generate a skeleton image of the probable nuclear locations.

24. The detector according to claim 23, wherein the thinning process comprises a Hilditch thinning process.

* * * * *